US00RE40752E

(19) United States
(12) Reissued Patent
Himelfarb et al.

(10) Patent Number: US RE40,752 E
(45) Date of Reissued Patent: Jun. 16, 2009

(54) DIENE REMOVAL FROM AN OLEFIN FEEDSTOCK

(75) Inventors: Paul B. Himelfarb, Houston, TX (US); Cornelius Mark Bolinger, Sugarland, TX (US)

(73) Assignee: Shell Oil Company, Houston, TX (US)

(21) Appl. No.: 10/318,718

(22) Filed: Dec. 13, 2002

Related U.S. Patent Documents

Reissue of:
(64) Patent No.: 6,388,162
Issued: May 14, 2002
Appl. No.: 09/566,462
Filed: May 8, 2000

(51) Int. Cl.
*C07C 5/03* (2006.01)
*C07C 7/63* (2006.01)

(52) U.S. Cl. ..... 585/809; 585/254; 585/260; 585/261; 585/262

(58) Field of Classification Search ..... 585/809, 585/254, 260, 261, 262
See application file for complete search history.

(56) References Cited

U.S. PATENT DOCUMENTS

| | | | | |
|---|---|---|---|---|
| 3,674,886 | A | 7/1972 | Komatsu et al. | |
| 3,676,523 | A | 7/1972 | Mason et al. | |
| 3,686,351 | A | 8/1972 | Mason et al. | |
| 3,737,475 | A | 6/1973 | Mason et al. | |
| 3,770,619 | A | 11/1973 | Derrien et al. | |
| 3,787,514 | A | 1/1974 | Bernusset | 260/677 H |
| 3,825,615 | A | 7/1974 | Lutz | |
| 4,020,121 | A | 4/1977 | Kister et al. | |
| 4,076,842 | A | 2/1978 | Plank et al. | |
| 4,351,980 | A | 9/1982 | Reusser et al. | |
| 4,551,443 | A | 11/1985 | Hudson | |
| 4,717,785 | A | 1/1988 | Paxson | |
| 4,762,956 | A | 8/1988 | Liu et al. | 585/259 |
| 5,072,057 | A | 12/1991 | Oswald et al. | |
| 5,112,519 | A | 5/1992 | Giacobbe et al. | |
| 5,376,393 | A | 12/1994 | Nardelli et al. | |
| 5,378,439 | A | 1/1995 | Delobel et al. | |
| 5,510,306 | A | 4/1996 | Murray | |
| 5,780,694 | A | 7/1998 | Singleton | |
| 5,849,960 | A | 12/1998 | Singleton et al. | |
| 5,994,591 | A | 11/1999 | Arnoldy et al. | |
| 6,084,140 | A | 7/2000 | Kitamura et al. | |

FOREIGN PATENT DOCUMENTS

| | | |
|---|---|---|
| EP | 0903333 A1 | 7/1998 |
| EP | 0 903 333 A1 | 3/1999 |
| FR | 1237412 | 6/1960 |
| JP | 5379803 | 7/1978 |
| JP | 56150022 | 11/1981 |

OTHER PUBLICATIONS

U.S. Appl. No. 09/566,460, filed May 8, 2000, Murray, et al.
U.S. Appl. No. 10/216,522, filed Aug. 8, 2000, Murray, et al.
U.S. Appl. No. 09/566,461, filed May 8, 2000, Murray, et al.
U.S. Appl. No. 09/566,463, filed May 8, 2000, Murray, et al.
"A Method for the Catalytic Oligomerization of Monoolefins", Research Disclosure, Kenneth Mason Publications, Hamsphire, GB No. 415, Nov. 1998, pp. 1445–1451, XP000824939.
"Sasol Detergent Alcohols", Preliminary Sasol R&D Technical Bulletin; Oct. 1995.

*Primary Examiner*—Thuan Dinh Dang

(57) ABSTRACT

The invention pertains to a process of removing dienes from an olefin feedstock. A preferred olefin feedstock is for the production of primary alcohol compositions by skeletal isomerization of the olefins followed by hydroformylation. In this preferred embodiment, the olefin feedstock may be purified before and/or after skeletal isomerization. The olefins in the feedstock preferably have a carbon chain length of about 8 to about 36 carbon atoms, preferably about 10 to about 20 carbon atoms, most preferably about 12 to about 18 carbon atoms.

87 Claims, No Drawings

DIENE REMOVAL FROM AN OLEFIN FEEDSTOCK

Matter enclosed in heavy brackets [ ] appears in the original patent but forms no part of this reissue specification; matter printed in italics indicates the additions made by reissue.

FIELD OF THE INVENTION

The invention pertains to a process of removing dienes from an olefin feedstock. A preferred olefin feedstock is for the production of primary alcohol compositions by skeletal isomerization of the olefins followed by hydroformylation. The olefin feedstock may be purified before and/or after skeletal isomerization. The olefins in the feedstock preferably have a carbon chain length of about 8 to about 36 carbon atoms, preferably about 10 to about 20 carbon atoms, most preferably about 12 to about 18 carbon atoms.

BACKGROUND OF THE INVENTION

Alcohols of long chain olefins having about 10 to 28 carbon atoms have considerable commercial importance in a variety of applications, including detergents, soaps, surfactants, and freeze point depressants in lubricating oils. These alcohols are produced by a number of commercial processes, such as by oxo or hydroformylation of long chain olefins. Typical commercially available long chain alcohols are the NEODOL® alcohols available from Shell Chemical Company, the EXXAL® alcohols available from Exxon Chemical Company, and the LIAL® alcohols available from Enichem.

In the manufacture of the NEODOL® alcohols, a redominantly linear olefin feed is subjected to hydroformylation by reacting carbon monoxide and hydrogen onto the olefin in the presence of an oxo catalyst to form an alcohol. Over 80% of the alcohol molecules in the resulting alcohol are linear primary alcohols. Of the branched primary alcohols in the composition, most, if not all of the branching is on the C2 carbon atom relative to the hydroxyl bearing carbon atom. These alcohols subsequently can be converted to anionic or nonionic detergents or general surfactants by sulfonation or ethoxylation of the alcohol, or by conversion of the alcohol to an alcohol-ethoxysulfate.

The NEODOL® alcohols are commercially successful intermediates to the production of detergents. One reason for this success undoubtedly is that the NEODOL® alcohols are economically produced with high yields of linear alcohols. The sulfonates of linear alcohols are more biodegradable than the sulfonates of branched long chain alcohols. Since detergents and soaps used by consumers for washing ultimately are released into the environment, the need for surfactants or detergents with maximal biodegradability is well recognized.

The highly linear NEODOL® alcohols have the advantage of a high level of biodegradability; however, the high degree of linearity of these alcohols also increases their hydrophobicity, thereby decreasing their cold water solubility/detergency. Government regulations call for both increased biodegradability and increased solubility.

Alcohols that have been found to meet both the biodegradability and the solubility government standards are branched primary alcohols (and their sulfate derivatives): having about 8 to about 36 carbon atoms; having an average number of branches per molecular chain of at least 0.7 (defined below); having less than 0.5 atom % of quaternary carbon atoms; and, having at least methyl and ethyl branching. These alcohols, as well as a method for preparing them, are described in U.S. Pat. No. 5,849,960, incorporated herein by reference. The method basically involves contacting a feed comprising linear olefins having 7 to 35 carbon atoms with a skeletal isomerization catalyst, and converting the resulting skeletally isomerized olefin to a saturated branched primary alcohol, preferably by hydroformylation.

Unfortunately, olefin feedstreams have been found to contain at least some level of dienes. Dienes can lower the catalytic performance of many commonly used catalysts, such as those used for skeletal isomerization of olefins and those used for hydroformylation.

SUMMARY OF THE INVENTION

The present invention provides a method for purifying an olefin stream comprising: providing an olefin feedstock wherein the olefins have an average molecular chain length of from about 8 to about 32 carbon atoms, the olefin feedstock comprising a first quantity of dienes; and, contacting the olefin feedstock with a hydrogenation catalyst and a gas feed comprising hydrogen at a feedstock flow rate and under conditions effective to reduce the first quantity of dienes to a second quantity of dienes without substantially increasing final paraffin content in the olefin feedstock.

DETAILED DESCRIPTION OF THE INVENTION

Typical olefin feedstocks comprise from about 100 to about 2000 ppm dienes. The invention pertains to a method for removing these dienes or, more specifically, for selectively converting these dienes to olefins with minimal production of paraffins.

Olefin feedstocks from substantially any source may be treated according to the invention to remove dienes. The invention is not limited to the treatment of olefin feedstocks which are to be subjected to skeletal isomerization and/or to hydroformylation. However, preferred feedstocks are olefin feedstocks which are to be subjected to skeletal isomerization and/or to hydroformylation to produce branched primary alcohols such as those produced in U.S. Pat. No. 5,849,960, incorporated herein by reference. With respect to the process described in that patent, the olefin feedstock may be treated to remove or convert dienes either before or after skeletal isomerization. The method preferably converts about 60 wt. % or more of the dienes to olefins without producing more than about 1 wt. % paraffins.

In order to accomplish the required selective conversion of dienes to olefins, one of the unsaturated carbon-carbon bonds in the dienes is selectively hydrogenated, leaving a monoolefin. The invention accomplishes this selective hydrogenation by feeding the olefin feedstock at a relatively slow (trickle flow) rate to a known, selective hydrogenation catalyst in the presence of a reduced hydrogen content reaction gas.

Any suitable low activity/high selectivity (or "mild") hydrogenation catalyst may be used. Suitable catalysts typically comprise, on a suitable support, a metal selected from Groups 9, 10, or 11 of the Periodic Table of the Elements, F, Cotton et al. Advanced Inorganic Chemistry (Fifth Ed. 1998). Preferred metals for use as a catalytic agent in the present process are Co, Ni, Pd, and Pt, most preferably palladium, either alone or alloyed with Ag, Cu, Co, and combinations thereof. The reactivity of the catalyst may be reduced to achieve selectivity by using less of a more active metal on the support or by using a less reactive metal. Where palladium is used as the catalytic agent, the concentration of palladium on a support is from about 0.05 to about 0.5 wt. %, preferably about 0.05 to about 0.2 wt. %.

Examples of suitable supports for the catalytic metal include, but are not necessarily limited to aluminas, silicas, molecular sieves, activated carbon, aluminosilicate clays, and amorphous silicoaluminas, preferably alumna, silica and carbon. Most preferred support materials are alumina and silica. Preferred supports have up to about 15 $m^2/g$ surface area, and preferably have from about 2 to about 5 $m^2/g$ surface area. A most preferred catalyst for use in the present invention comprises palladium on an alumina support.

The catalyst may or may not be modified using a suitable promoter, such as chromium, barium, or lanthanium. A preferred promoter is chromium at a preferred concentration of from about 0.05 to about 0.2 wt. %, preferably about 0.05 wt. %. When chromium is used as a promoter, other suitable additives which may be used at from about 0.05 to 0.25 wt %, preferably about 0.05 wt %, include, but are not necessarily limited to Ba, La, Dy, Ce, Nb, or Sm, preferably Ba or La. A preferred commercially available catalyst is K-8327, a palladium on aluminum catalyst available from W.C. Heraeus GmbH, Catalyst Department PKT, Heraeusstrasse 12-1, D-63450 Hanau, Germany.

Surprisingly, the catalysts preferably are used in a fixed bed trickle flow reaction mode at low feed flow. Persons of ordinary skill in the art would expect that a relatively long exposure time between the feedstock and the catalyst in a trickle flow mode would result in more hydrogenation and an undesirably high production of paraffins in the product. The longer the feedstock is exposed to the catalyst, the more selective the process is to the production of olefins. This is particularly true at a low gas flow and when the level of hydrogen in the reaction gas is limited, preferably to from about 2 to about 6 vol. %, with the remainder being an inert gas, preferably nitrogen. In other words, the longer the exposure to the catalyst and to a reaction gas having a limited hydrogen content, the higher the conversion of dienes, and the lower the yield of paraffins.

The reaction conditions are relatively mild. The olefin feedstock preferably is fed to the fixed bed at about 1 liquid hourly space velocity (LHSV) or less, most preferably about 0.25 to 0.5 LHSV. The reaction pressure may be ambient and is not critical, but preferably is maintained relatively low, from about 20 to about 200 psig, most preferably about 30 psig. The reaction temperature also preferably is relatively low, from about 0° C. (32° F.) to about 100° C. (212° F.), preferably from about 26° C. (80° F.) to about 49° C. (120° F.), most preferably about 38° C. (100.40° F.).

Without limiting the invention to any particular mechanism of action, the longer reaction time is believed to give the bulkier, more branched dienes more time to diffuse into the catalyst so that more of the branched dienes are selectively hydrogenated. As to the conversion reaction itself, alpha unsaturated bonds are known to be more reactive than internal unsaturated bonds, particularly when those bonds are conjugated with a second unsaturated bond. Because of this, the non-conjugated dienes are believed to convert to conjugated dienes, and the more reactive, conjugated unsaturated bond is believed to be preferentially hydrogenated.

Olefin feedstocks produced by any number of techniques may be treated according to the present invention. As already stated, the olefins in the feedstock have an average chain length of about 8 to about 36 carbon atoms, preferably at least about 10 to about 20 carbon atoms, most preferably about 12 to about 18 carbon atoms. $C_8$ to $C_{36}$ olefins have a variety of uses, including but not necessarily limited to uses in paper processing, drilling fluids, and machine or metal working. In a preferred embodiment, the olefin feedstock is either the stream to be skeletally isomerized, or the stream produced by skeletal isomerization in the method for producing the primary alcohols described in U.S. Pat. No. 5,849,960, incorporated herein by reference.

The skeletal isomerization catalyst contains a zeolite having at least one channel with a crystallographic free channel diameter ranging from greater than 4.2 Å and less than 7 Å., measured at room temperature, with essentially no channel present which has a free channel diameter which is greater than 7 Å. Suitable zeolites are described in detail in U.S. Pat. No. 5,849,960, which has been incorporated herein by reference. Examples of zeolites, including molecular sieves, that can be used in the processes with a channel size between about 0.42 nm and 0.7 nm, include ferrierite, AlPO-31, SAPO-11, SAPO-31, SAPO-41, FU-9, NU-10, NU-23, ZSM-12, ZSM-22, ZSM-23, ZSM-35, ZSM-48, ZSM-50, ZSM-57, SUZ-4, SUZ-4A, SMO3, DAF-1, MeAPO-11, MeAPO-31, MeAPO-41, MeAPSO-11, MeAPSO-31, and MeAPSO-41, MeAPSO-46, ELAPO-11, ELAPO-31, ELAPO-41, ELAPSO-11, ELAPSO-31, and ELAPSO-41, laumontite, cancrinite, offretite, hydrogen form of stilbite, the magnesium or calcium form of mordenite and partheite.

Particularly preferred zeolites are those having the ferrierite isotypic framework structure (or homeotypic). See the Atlas of Zeolite Structure Types, by W. M. Meier and D. H. Olson, published by Butterworth-Heinemann, third revised edition, 1992, page 98. The prominent structural features of ferrierite found by x-ray crystallography are parallel channels in the alumino-silicate framework which are roughly elliptical in cross-section. Examples of such zeolites having the ferrierite isotypic framework structure include natural and synthetic ferrierite (can be orthorhombic or monoclinic), Sr-D, FU-9 (EP B-55,529), ISI-6 (U.S. Pat. No. 4,578,259), NU-23 (E.P.A-103,981), ZSM-35 (U.S. Pat. No. 4,016,245) and ZSM-38 (U.S. Pat. No. 4,375,573). A preferred skeletal isomerization catalyst for use in conjunction with the present invention is a hydrogen ferrierite catalyst, as described in U.S. Pat. No. 5,510,306, incorporated herein by reference.

Diene removed may occur prior to skeletal isomerization and/or prior to hydroformylation in this procedure. Hydroformylation is a term used in the art to denote the reaction of an olefin with CO and $H_2$ to produce an aldehyde/alcohol which has one more carbon atom then the reactant olefin. Frequently, the term hydroformylation is utilized to cover the aldehyde and the reduction to the alcohol step in total, i.e., hydroformylation refers to the production of alcohols from olefins via carbonylation and an aldehyde reduction process. As used herein, hydroformylation refers to the ultimate production of alcohols.

Illustrative hydroformylation catalysts include, but are not necessarily limited to, cobalt hydrocarbonyl catalysts and metal-phosphine ligands comprising metals including, but not necessarily limited to palladium, cobalt, and rhodium. The choice of catalysts determines the various reaction conditions imposed, including whether diene removal is advisable. Certain catalysts are not as susceptible to diene poisoning as others. In a preferred embodiment, diene removal is used in conjunction with palladium based catalysts, including, but not necessarily limited to palladium—phosphine ligand catalysts. One of ordinary skill in the art, by referring to any of the well-known literature on oxo alcohols, can readily determine the conditions of temperature and pressure that will be needed to hydroformylate the olefins. An example in addition to U.S. Pat. No. 5,849,960 is EP 0 903 333 A1, incorporated herein by reference.

The invention will be better understood with reference to the following examples, which are illustrative only and should not be construed to limit the invention to a particular embodiment.

EXAMPLE I

A conventional type catalyst used for removing dienes in pyrolysis gasoline(-carbon $C_5$–$C_{10}$) was used to determine hydrogenation specificity. The catalyst employed contained (0.5 wt % Pd on alumina). The catalyst was used in a trickle-flow reactor at 38° C. (100° F.), 5 kPa (30 psig), with 25 cc catalyst using a $C_{13}/C_{14}$ liner olefin feed with approximately 500 ppm dienes.

| Hydrogen (1/hr) | Dienes Removed (% conversion) | Paraffin Make Wt % |
|---|---|---|
| 3.80 | 55 | 13.6 |
| 0.20 | 34 | 7.9 |
| 0.14 | 28 | 6.6 |
| 0.02 | 18 | 0.3 |

Although it appears that target diene removal can be reached, the removal does not appear to be sufficiently selective. At low hydrogen flows, to minimize paraffin make, diene removal was not sufficient. It was decided that a more selective catalyst is required.

EXAMPLE II

A batch reactor was used to screen a number of different catalysts under the following conditions: 500 ml reactor; 350 ml $C_{13}/C_{14}$ linear olefin feed; 38.33 kPa (230 psig) with 6% $H_2$ in $N_2$; 1000 rpm; ~24° C. (75° F.). Representative results (paraffin make) are given below for 40% diene removal.

| Catalyst | Volume Cat Cc | Surface Area m2/g | Pd Loading wt % | Paraffin Make wt % |
|---|---|---|---|---|
| HEREAUS CHP-13 ™ | 9 | 110 | 0.4 | 1.2 |
| CALSIRAT E144 ™ | 9 | 40 | 0.5 | 0.9 |
| HEREAUS K8327 ™ | 9 | 5 | 0.2 | 0.5 |
| In-house 1 | 9 | 14 | 0.05 | 0.7 |
| In-house 2 | 30 | 10 | 0.05 | 0.5 |
| In-house 3 | 30 | 6 | 0.05 | 0.3 |

Increased selectivity (lower paraffin make) was obtained with low surface area <15$M^2$/2g and lower Pd loading <0.5 wt %. The in-house developed catalysts were promoted with chromium (0.05 wt %), as described in U.S. Pat. No. 4,551,443, incorporated herein by reference, using 0.05 wt. % Ba as an additive.

Of the commercial catalysts tested, HEREAUS K8327 gave the best results. The catalyst was used in subsequent process optimization in continuous operation and commercialization studies, although any of the in-house developed catalysts would be suitable.

EXAMPLE III

Once Hereaus K8327 was identified as a suitable commercially available catalyst, process conditions were varied to optimally balance activity and selectivity. The effect of hydrogen flow (GHSV-gas hourly space velocity) for $C_{13}/C_{14}$ and $C_{11}/C_{12}$ linear feeds is given below, where the hydrogen was diluted with nitrogen in (6% $H_2/N_2$). (GHSV is defined as the vol. feed/vol. cat. hr.). The range of hydrogen dilution ranged from 2% to 6% and 6% was found preferred. For the $C_{11}/C_{12}$ example, the results are given for two different feed flows of WHSV equal 2 and 1. (The WHSV is defined by g. feed/g. cat. hr).

C13/C14 Feed, WHSV=2:

| GHSV hr-1 | Diene Conv. % | Paraffin Make Wt % |
|---|---|---|
| 15 | 26 | 0.6 |
| 30 | 32 | 0.7 |
| 35 | 35 | 0.8 |
| 45 | 32 | 1.1 |
| 75 | 35 | 1.4 |

C11/C12 Feed, WHSV=2:

| GHSV hr-1 | Diene Conv. % | Paraffin Make Wt % |
|---|---|---|
| 12 | 31 | 0.36 |
| 25 | 39 | 0.59 |
| 45 | 47 | 0.83 |

C11/C12 Feed, WHSV=1:

| GHSV hr-1 | Diene Conv. % | Paraffin Make Wt % |
|---|---|---|
| 8 | 55 | 0.4 |
| 25 | 53 | 1.1 |

Results from the $C_{13}/C_{14}$ feed show that there is an optimal gas flow, above which excess paraffins are made with no significant increase in diene removal. The optimal gas flow also depends on the type of feed used, as shown later. Under the condition above at GHSV equal to 35 for the $C_{13}/C_{14}$ feed, a longer-term test was performed to check catalyst stability. The test run was carried out for approximately 2000 hr with no significant catalyst performance change.

Results show that dienes are more easily and selectively removed from the $C_{11}/C_{12}$ feeds than from the $C_{13/C14}$ feed. One factor affecting activity is the concentration of alpha olefins (AO's), as compared to internal olefins. High AO feeds (~20–50%) typically had about 10–20% less diene removal respectively and the $C_{11}/C_{12}$ feed had the lowest AO content (~6%).

The use of lower feed flows combined with lower gas flows resulted in an activity improvement and a dramatic selectivity improvement.

EXAMPLE IV

Initial results on branched feeds are shown below, as determined in a batch reactor. (The conditions of the batch reactor were the same as those given for linear feeds with the Heraeus K8327 catalyst). The feed contained approximately 520 ppm dienes. The results are broken-out depending on the carbon number, as shown below.

| | Total Dienes | C15-C16 Component | C8-C14 Component |
|---|---|---|---|
| Diene Removal % | 61% | 49% | 90% |

From the foregoing results, it appears that dienes can be effectively removed from branched feeds as well as linear feeds. The lighter dienes were removed more easily than the heavy dienes. (Note that by topping the feed, or separating the different olefins based on their carbon number, the lighter components were removed to the degree desired, as is done in the commercial process).

EXAMPLE V

Diene removal was performed in a continuous trickle flow reactor at the GHSV (G) and WHSV (W) shown below, along with the results:

| Reactor Conditions | Total Dienes Removed % | C15-C16 Dienes Removed % | C8-C14 Dienes Removed % | Paraffin make wt % |
|---|---|---|---|---|
| W = 2/G = 35 | 52 | 34 | 77 | 0.4 |
| W = 2/G = 45 | 49 | 35 | 72 | 0.5 |
| W = 1/G = 10 | 56 | 38 | 80 | 0.4 |
| W = 1/G = 20 | 70 | 48 | 76 | 0.5 |

The results demonstrate effective diene removal with minimal paraffin make with the branched olefin feed. Increased diene removal was obtained at lower feed flows, and in this regime the paraffin make was controlled to the desired low level by minimizing the gas flow. Further results were obtained with a topped-branched feed as a function of feed flow as shown below.

| WHSV | Diene Removal % |
|---|---|
| 2 | 32 |
| 1 | 45 |
| 0.5 | 64 |
| 0.25 | 74 |

These results further demonstrate increased diene removal at low feed rates. From the foregoing, it was determined that a WHSV of 0.5 would balance paraffin make (0.5 wt %) and the need to remove only the most active dienes from the feed.

Persons of ordinary skill in the art will recognize that many modifications may be made to the present invention without departing from the spirit and scope of the present invention. The embodiment described herein is meant to be illustrative only and should not be taken as limiting the invention, which is defined in the following claims.

We claim:

1. A method for purifying an olefin stream comprising:

providing an olefin feedstock wherein said olefins have an average molecular chain length of from about 10 to about 20 carbon atoms, said olefin feedstock comprising a quantity of dienes;

contacting said olefin feedstock with a hydrogenation catalyst that is sensitive to diene poisoning in the presence of a gas feed comprising an inert gas, said gas feed also comprising from about 2 to about 6 vol. % hydrogen, at a feedstock flow rate of about 1 LHSV or less under conditions effective to convert a majority of said dienes to olefins.

2. The method of claim 1 wherein said hydrogenation catalyst comprises a fixed bed.

3. The method of claim 1 wherein said hydrogenation catalyst comprises palladium.

4. The method of claim 1 wherein said hydrogenation catalyst comprises palladium.

5. The method of claim 1 wherein said hydrogenation catalyst comprises about 0.2 wt. % palladium on a support.

6. The method of claim 2 wherein said hydrogenation catalyst comprises about 0.2 wt. % palladium on a support.

7. The method of claim 1 wherein said hydrogenation catalyst comprises a support comprising alumina having a surface area of from about 2 to about 5 $m^2/g$.

8. The method of claim 2 wherein said hydrogenation catalyst comprises a support comprising alumina having a surface area of from about 2 to about 5 $m^2/g$.

9. The method of claim 3 wherein said hydrogenation catalyst comprises a support comprising alumina having a surface area of from about 2 to about 5 $m^2/g$.

10. The method of claim 4 wherein said hydrogenation catalyst comprises a support comprising alumina having a surface area of from about 2 to about 5 $m^2/g$.

11. The method of claim 5 wherein said support comprises alumina having a surface area of from about 2 to about 5 $m^2/g$.

12. The method of claim 6 wherein said support comprises alumina having a surface area of from about 2 to about 5 $m^2/g$.

13. The method of claim 1 wherein said feedstock flow rate is about 0.5 LHSV or less.

14. The method of claim 2 wherein said feedstock flow rate is about 0.5 LHSV or less.

15. The method of claim 3, wherein said feedstock flow rate is about 0.5 LHSV or less.

16. A method for purifying an olefin stream comprising:

providing an olefin feedstock wherein said olefins have an average molecular chain length of from about 8 to about 36 carbon atoms, said olefin feedstock comprising a quantity of dienes;

contacting said olefin feedstock and a gas feed comprising an inert gas with a hydrogenation catalyst that is sensitive to diene poisoning under conditions effective to produce a purified olefin stream comprising a paraffin content of about 1 wt.% or less, said conditions comprising a quantity of hydrogen in said gas feed of from about 2 to about 6 vol. % and a flow rate of said olefin feedstock, said quantity and said flow rate being sufficiently low to convert a majority of said dienes to olefins.

17. The method of claim 16 wherein said average molecular chain length is about 10 carbon atoms or more.

18. The method of claim 16 wherein said hydrogenation catalyst comprises a fixed bed.

19. The method of claim 17 wherein said hydrogenation catalyst comprises a fixed bed.

20. The method of claim 16 wherein said hydrogenation catalyst comprises palladium.

21. The method of claim 17 wherein said hydrogenation catalyst comprises palladium.

22. The method of claim 18 wherein said hydrogenation catalyst comprises palladium.

23. The method of claim 19 wherein said hydrogenation catalyst comprises palladium.

24. The method of claim 16 wherein said hydrogenation catalyst comprises about 0.2 wt. % palladium on a support.

25. The method of claim 17 wherein said hydrogenation catalyst comprises about 0.2 wt. % palladium on a support.

26. The method of claim 16 wherein said hydrogenation catalyst comprises a support comprising alumina having a surface area of from about 2 to about 5 $m^2/g$.

27. The method of claim 19 wherein said hydrogenation catalyst comprises a support comprising alumina having a surface area of from about 2 to about 5 $m^2/g$.

28. The method of claim 16 wherein said feedstock flow rate is about 1 LHSV or less.

29. The method of claim 17 wherein said feedstock flow rate is about 1 LHSV or less.

30. The method of claim 18 wherein said feedstock flow rate is about 1 LHSV or less.

31. The method of claim 19 wherein said feedstock flow rate is about 1 LHSV or less.

32. The method of claim 20 wherein said feedstock flow rate is about 1 LHSV or less.

33. The method of claim 21 wherein said feedstock flow rate is about 1 LHSV or less.

34. The method of claim 22 wherein said feedstock flow rate is about 1 LHSV or less.

35. The method of claim 23 wherein said feedstock flow rate is about 1 LHSV or less.

36. The method of claim 16 wherein said feedstock flow rate is about 0.5 LHSV or less.

37. The method of claim 17 wherein said feedstock flow rate is about 0.5 LHSV or less.

38. The method of claim 18 wherein said feedstock flow rate is about 0.5 LHSV or less.

39. The method of claim 19 wherein said feedstock flow rate is about 0.5 LHSV or less.

40. The method of claim 20 wherein said feedstock flow rate is about 0.5 LHSV or less.

41. The method of claim 21 wherein said feedstock flow rate is about 0.5 LHSV or less.

42. The method of claim 22 wherein said feedstock flow rate is about 0.5 LHSV or less.

43. The method of claim 23 wherein said feedstock flow rate is about 0.5 LHSV or less.

44. The method of claim 16 wherein said method produces a purified olefin stream comprising about 40% of said quantity of dienes or less.

45. The method of claim 17 wherein said method produces a purified olefin stream comprising about 40% of said quantity of dienes or less.

46. The method of claim 18 wherein said method produces a purified olefin stream comprising about 40% of said quantity of dienes or less.

47. The method of claim 19 wherein said method produces a purified olefin stream comprising about 40% of said quantity of dienes or less.

48. The method of claim 20 wherein said method produces a purified olefin stream comprising about 40% of said quantity of dienes or less.

49. The method of claim 21 wherein said method produces a purified olefin stream comprising about 40% of said quantity of dienes or less.

50. The method of claim 22 wherein said method produces a purified olefin stream comprising about 40% of said quantity of dienes or less.

51. The method of claim 23 wherein said method produces a purified olefin stream comprising about 40% of said quantity of dienes or less.

52. A method for purifying an olefin stream comprising:

providing an olefin feedstock wherein said olefins have an average molecular chain length of from about 10 to about 20 carbon atoms and an average number of branches per molecular chain of at least 0.7, said olefin feedstock comprising a quantity of dienes;

contacting said olefin feedstock with a fixed bed hydrogenation catalyst in the presence of a gas feed comprising an inert gas, said gas feed also comprising from about 2 to about 6 vol. % hydrogen, said hydrogenation catalyst comprising from about 0.05 wt. % to about 0.2 wt. % palladium on alumina, said alumina having a surface area of about 15 $m^2/g$ or less, wherein said olefin feedstock has a flow rate through said fixed bed of about 1 LHSV or less under conditions effective to convert a majority of said dienes to olefins.

53. The method of claim 52 wherein said alumina has a surface area of about 2 to about 5 $m^2/g$.

54. The method of claim 52 wherein said hydrogenation catalyst comprises about 0.2 wt. % palladium.

55. The method of claim 53 wherein said hydrogenation catalyst comprises about 0.2 wt. % palladium.

56. The method of claim 52 wherein said feedstock flow rate is about 0.5 LHSV or less.

57. The method of claim 53 wherein said feedstock flow rate is about 0.5 LHSV or less.

58. The method of claim 54 wherein said feedstock flow rate is about 0.5 LHSV or less.

59. The method of claim 55 wherein said feedstock flow rate is about 0.5 LHSV or less.

60. The method of claim 52 wherein said method produces a purified olefin stream comprising about 40% of said quantity of dienes or less and a paraffin content of about 1 wt. % or less.

61. The method of claim 53 wherein said method produces a purified olefin stream comprising about 40% of said quantity of dienes or less and a paraffin content of about 1 wt. % or less.

62. The method of claim 54 wherein said method produces a purified olefin stream comprising about 40% of said quantity of dienes or less and a paraffin content of about 1 wt. % or less.

63. The method of claim 55 wherein said method produces a purified olefin stream comprising about 40% of said quantity of dienes or less and a paraffin content of about 1 wt. % or less.

64. The method of claim 56 wherein said method produces a purified olefin stream comprising about 40% of said quantity of dienes or less and a paraffin content of about 1 wt. % or less.

65. The method of claim 57 wherein said method produces a purified olefin stream comprising about 40% of said quantity of dienes or less and a paraffin content of about 1 wt. % or less.

66. The method of claim 58 wherein said method produces a purified olefin stream comprising about 40% of said quantity of dienes or less and a paraffin content of about 1 wt. % or less.

67. The method of claim 59 wherein said method produces a purified olefin stream comprising about 40% of said quantity of dienes or less and a paraffin content of about 1 wt. % or less.

*68. A method for purifying an olefin stream comprising:*

*providing an olefin feedstock wherein said olefins have an average molecular chain length of from about 8 to about 36 carbon atoms, said olefin feedstock comprising a quantity of dienes;*

*contacting said olefin feedstock with a hydrogenation catalyst that is sensitive to diene poisoning in the presence of a gas feed comprising an inert gas, said gas feed also comprising from about 2 to about 6 vol. % hydrogen at a feedstock flow rate and under conditions effective to convert a majority of said dienes to olefins.*

*69. The method of claim 68 wherein said hydrogenation catalyst comprises a fixed bed.*

*70. The method of claim 69 wherein said hydrogenation catalyst comprises palladium.*

*71. The method of claim 68 wherein said hydrogenation catalyst comprises palladium.*

*72. The method of claim 69 wherein said hydrogenation catalyst comprises about 0.2 wt. % palladium on a support.*

*73. The method of claim 68 wherein said hydrogenation catalyst comprises about 0.2 wt. % palladium on a support.*

*74. The method of claim 69 wherein said hydrogenation catalyst comprises a support comprising alumina having a surface area of from about 2 to about 5 $m^2/g$.*

*75. The method of claim 70 wherein said hydrogenation catalyst comprises a support comprising alumina having a surface area of from about 2 to about 5 $m^2/g$.*

*76. The method of claim 71 wherein said hydrogenation catalyst comprises a support comprising alumina having a surface area of from about 2 to about 5 $m^2/g$.*

*77. The method of claim 72 wherein said hydrogenation catalyst comprises a support comprising alumina having a surface area of from about 2 to about 5 $m^2/g$.*

*78. The method of claim 68 wherein said support comprises alumina having a surface area of from about 2 to about 5 $m^2/g$.*

*79. The method of claim 69 wherein said feedstock flow rate is about 0.5 LHSV or less.*

*80. The method of claim 70 wherein said feedstock flow rate is about 0.5 LHSV or less.*

*81. The method of claim 71 wherein said feedstock flow rate is about 0.5 LHSV or less.*

*82. The method of claim 72 wherein said feedstock flow rate is about 0.5 LHSV or less.*

*83. The method of claim 69 wherein said average molecular chain length is about 10 carbon atoms or more.*

*84. The method of claim 70 wherein said average molecular chain length is about 10 carbon atoms or more.*

*85. The method of claim 69 wherein said feedstock flow rate is about 1 LHSV or less.*

*86. The method of claim 69 wherein said method produces a purified olefin stream comprising about 40% of said quantity of dienes or less.*

*87. The method of claim 68 wherein said method produces a purified olefin stream comprising about 40% of said quantity of dienes or less.*

* * * * *